(12) United States Patent
Watts et al.

(10) Patent No.: US 7,003,343 B2
(45) Date of Patent: Feb. 21, 2006

(54) METHOD AND APPARATUS FOR ANATOMICALLY TAILORED K-SPACE SAMPLING AND RECESSED ELLIPTICAL VIEW ORDERING FOR BOLUS-ENHANCED 3D MR ANGIOGRAPHY

(75) Inventors: Richard Watts, New York, NY (US); Yi Wang, Pittsburgh, PA (US); Martin R. Prince, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 409 days.

(21) Appl. No.: 10/109,888

(22) Filed: Apr. 1, 2002

(65) Prior Publication Data

US 2003/0032877 A1  Feb. 13, 2003

Related U.S. Application Data

(60) Provisional application No. 60/279,691, filed on Mar. 30, 2001.

(51) Int. Cl.
*A61B 5/05* (2006.01)
*G01V 3/00* (2006.01)

(52) U.S. Cl. .................. 600/410; 600/419; 324/306
(58) Field of Classification Search ............... 600/407, 600/410, 411, 412, 419, 436; 324/306, 307, 324/308, 309
See application file for complete search history.

(56) References Cited

U.S. PATENT DOCUMENTS

| | | | |
|---|---|---|---|
| 5,924,987 A | 7/1999 | Meaney et al. | |
| 6,144,873 A * | 11/2000 | Madore et al. | 600/410 |
| 6,242,914 B1 * | 6/2001 | Yoshitome | 324/309 |
| 6,289,232 B1 * | 9/2001 | Jakob et al. | 600/410 |
| 6,311,085 B1 | 10/2001 | Meaney et al. | |
| 6,487,435 B1 * | 11/2002 | Mistretta et al. | 600/420 |
| 6,745,064 B1 * | 6/2004 | Fuderer et al. | 600/410 |

OTHER PUBLICATIONS

Ho et al., "Peripheral Vascular Tree Stenoses: Evaluation with Moving-Bed Infusion-tracking MR Angiography,", *Radiology* (Mar. 1998), vol. 206, No. 3, pp 683-692.

Wang, et al., "Bolus-Chase MR Digital Subtraction Angiography in the Lower Extremity," *Radiology*, (1998) vol. 207, No. 1, pp. 263-269.

Meaney et al., "Stepping-Table Gadolinium-enhanced Digital Subtraction MR Angiography of the Aorta and Lower Extremity Arteries: Preliminary Experience," *Radiology*, (1999), vol. 211, No. 1, pp. 59-67.

(Continued)

*Primary Examiner*—Daniel Robinson
(74) *Attorney, Agent, or Firm*—Schwegman, Lundberg, Woessner & Kluth, P.A.

(57) ABSTRACT

Current bolus chase magnetic resonance angiography is limited by the imaging time for each station. Tailoring the density of k-space sampling along the anterior-posterior direction of the coronal station allows a substantial decrease in scan time that leads to greater contrast bolus sharing among stations and consequently a significant improvement in image quality. Fast arterial-venous transit in the carotid arteries requires accurate, reliable timing of the acquisition to the bolus transit to maximize arterial signal and minimize venous artifacts. The rising edge of the bolus is not utilized in conventional elliptical-centric view ordering because the critical k-space center must be acquired with full arterial enhancement. The invention provides a recessed elliptical-centric view ordering scheme is introduced in which the k-space center is acquired a few seconds following scan initiation. The recessed view ordering is shown to be more robust to timing errors in a patient studies.

13 Claims, 11 Drawing Sheets

OTHER PUBLICATIONS

Wang et al., "Timing Algorithm for Bolus Chase MR Digital Subtraction Angiography," *Magn Reson Med* (1998), vol. 39, No. 5, pp. 691-696.

Ho et al., "Automated Bolus Chase Peripheral MR Angiography: Initial Practical Experiences and Future Directions of This Work-In-Progress," *J. Magn. Reson Imaging*, (1999), vol. 10, No. 3, pp. 376-388.

Lee et al., "Dynamic k-Space Filling For Bolus Chase 3D MR Digital Subtraction Angiography," *Magn Reson Med*, (1998), vol. 40, No. 1, pp. 99-104.

Rofsky et al., "MR Angiography in the Evaluation of Atherosclerotic Peripheral Vascular Disease," *Radiology*, (2000), vol. 214, No. 2, pp. 325-338.

Grist, "MRA of the Abdominal Aorta and Lower Extremities," *J. Magn Reson Imaging*, (2000), vol. 11, No. 1, pp. 32-43.

Ho et al., "MR Angiography of Run-off Vessels," *Eur Radiol.* (1999), vol. 9, No. 7, pp. 1285-1289 (to be submitted in a supplemental IDS).

Ruhm et al., "Contrast-Enhanced 3D MR-Angiography of the Thorax, Abdomen and Lower Extremities," *Radiologe* (1999), vol. 39, No. 2, pp. 100-109 (to be submitted in a supplemental IDS).

Prince et al., "3D Contrast MR Angiography," *Springer*, Berlin (1999) (to be submitted in a supplemental IDS).

* cited by examiner

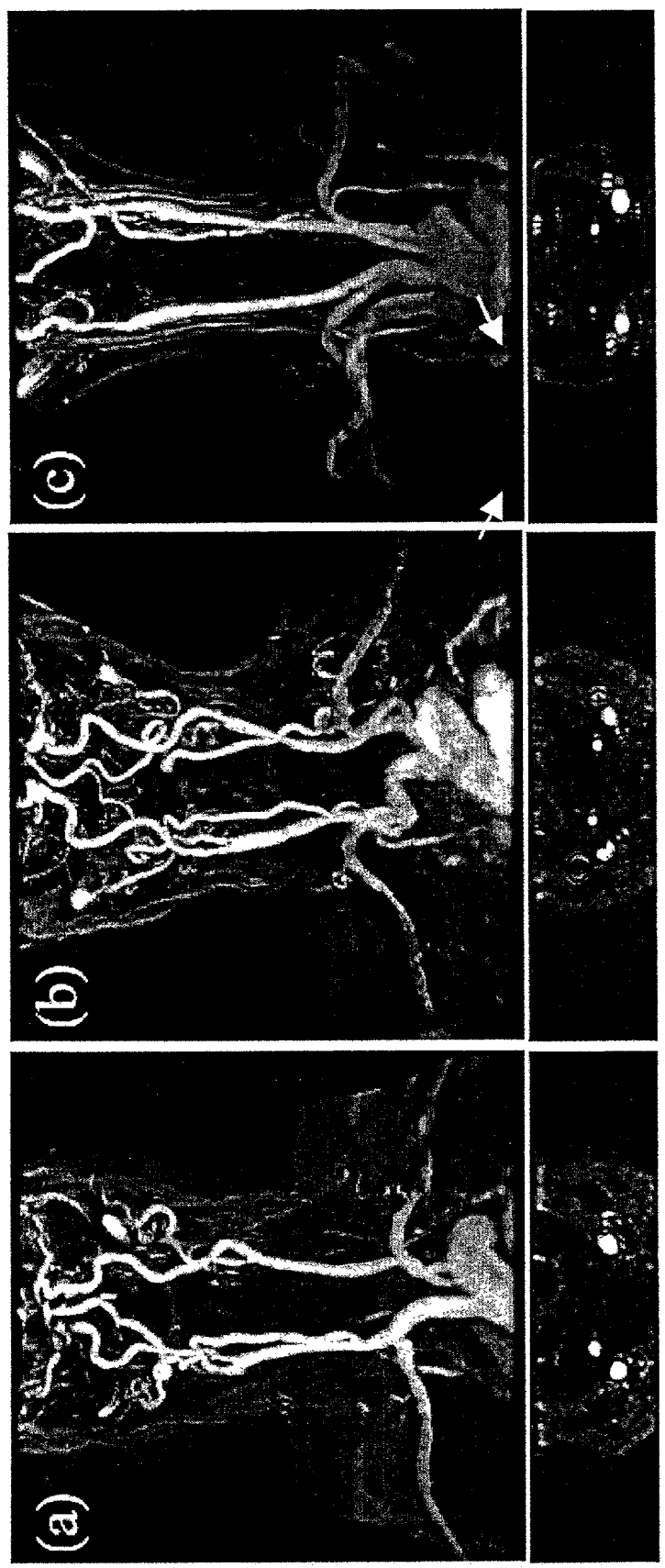

FIG. 10A
FIG. 10B
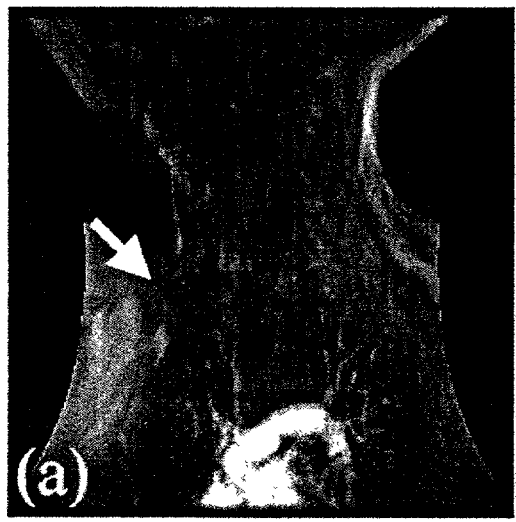
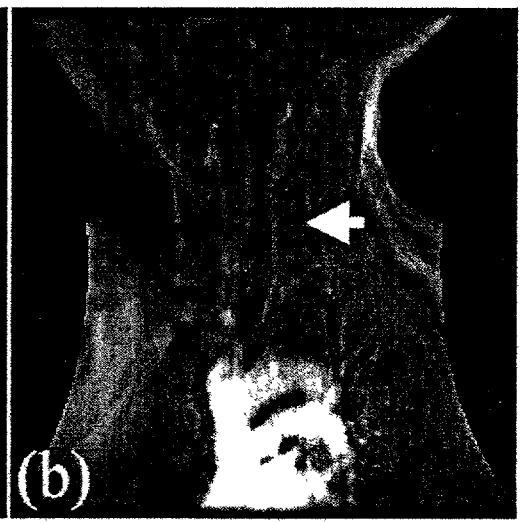
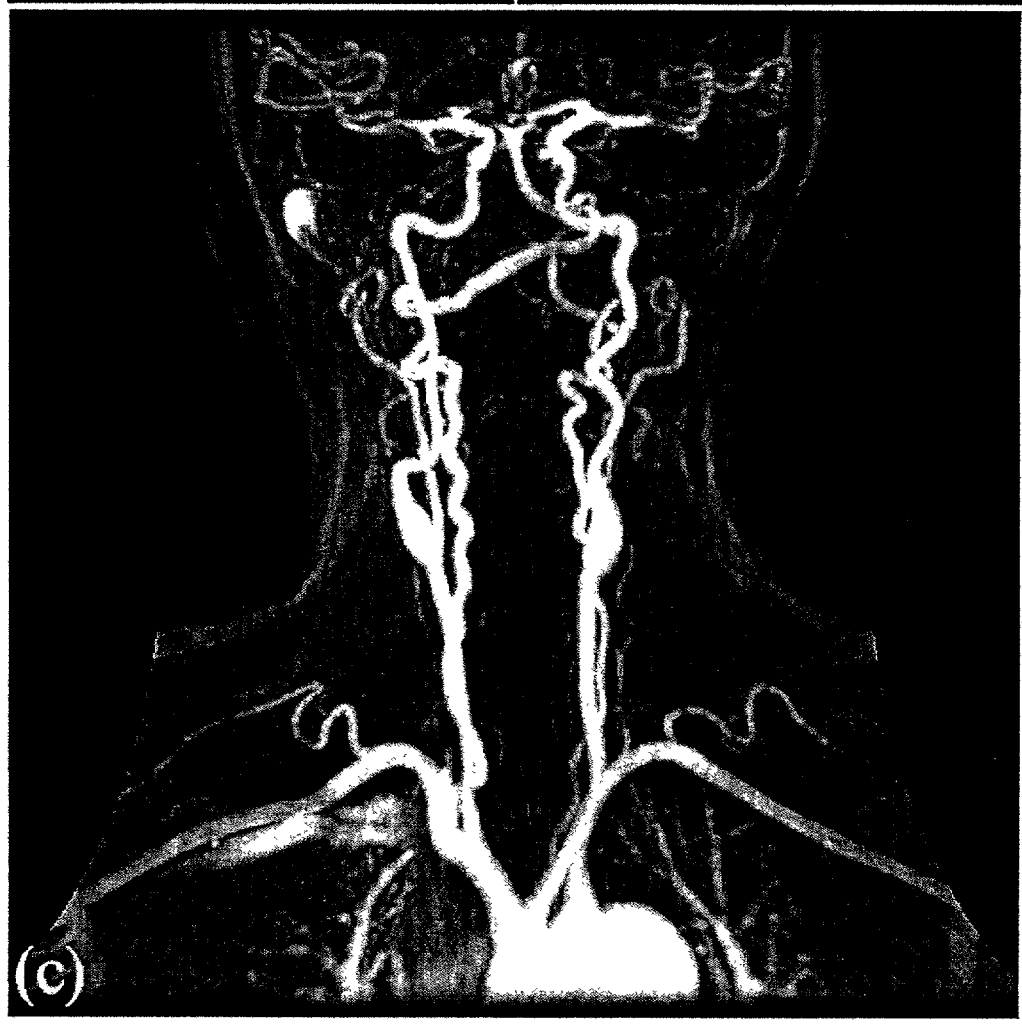
FIG. 10C

METHOD AND APPARATUS FOR ANATOMICALLY TAILORED K-SPACE SAMPLING AND RECESSED ELLIPTICAL VIEW ORDERING FOR BOLUS-ENHANCED 3D MR ANGIOGRAPHY

This application claims benefit to Provisional Application No. 60/279,691 filed Mar. 30, 2001; the disclosure of which is incorporated herein by reference.

The invention was made with government support under R01HL60879 by the National Institutes of Health. The government has certain rights in the invention.

FIELD OF INVENTION

The present invention relates to MR angiography using a reduced sample set to decrease the time needed to acquire image data for arterial features. As a result of the time reduction, the MR data acquisition can be performed in conjunction with the arrival and flow of a contrast agent through the arteries, thereby reducing the amount of contrast agent introduced in a patient. The invention further relates to method for acquiring MR to better delineate arterial features from a background and venous artifacts. In particular, modification of k-space view ordering more accurately times data acquisition to contrast arrival and peak contrast enhancement in a region of interest.

DESCRIPTION OF THE RELATED ART

Generally, contrast-enhanced MRA offers many advantages in imaging, including reduced flow artifacts and reduced scanning time.

In one application, bolus chase MR angiography has revolutionized imaging of peripheral vascular disease by allowing rapid imaging of the arterial anatomy of the entire lower half of the body with a single infusion of a gadolinium based contrast agent. This has been previously discussed in Meaney, J F M, Prince M R, *Floating Table Bolus Chase Peripheral Vascular MR Angiography*, U.S. Pat. No. 5,924, 987, issued Jul. 20, 1999; Ho K Y, Leiner T, de Haan M W, Kessels A G, Kitslaar P J, van Engelshoven J M., *Peripheral vascular tree stenoses: evaluation with moving-bed infusion-tracking MR angiograph;. Radiology* 1998; 206(3): 683–692; Wang Y, Lee H M, Khilnani N M, et al. *Bolus-chase MR digital subtraction angiography in the lower extremity. Radiology* 1998; 207(1):263–269; and Meaney J F, Ridgway J P, Chakraverty S, et al. *Stepping-table gadolinium-enhanced digital subtraction MR angiography of the aorta and lower extremity arteries: preliminary experience. Radiology* 1999; 211(1):59–67. Two strategies have emerged for obtaining arterial-phase images at three successive stations while avoiding excessive venous enhancement. One strategy is to image relatively slowly with a long infusion as further discussed in *Ho K Y, Leiner T, van Engelshoven J M. MR angiography of run-off vessels. Eur Radiol* 1999; 9(7):1285–1289. The infusion rate must be fast enough to give sufficient arterial enhancement but slow enough so that after extraction of gadolinium contrast in capillaries, venous enhancement is minimal. Typically an infusion rate of 0.3–0.5 ml/sec is suggested for an imaging duration of 45 seconds per station. However, there is little sharing of contrast dose between stations, and venous enhancement can still occur.

Another strategy is to image sufficiently rapidly to keep up with the contrast bolus so that the same bolus is imaged at all three stations. This has been discussed by Wang, et al as noted above and further in Wang Y, Lee H M, Avakian R, Winchester P A, Khilnani N M, Trost D., *Timing algorithm for bolus chase MR digital subtraction angiography. Magn Reson Med* 1998; 39(5):691–696 and Ho V B, Choyke P L, Foo T K, et al. *Automated bolus chase peripheral MR angiography: initial practical experiences and future directions of this work-in-progress. J Magn Reson Imaging* 1999; 10(3):376–388. Faster imaging allows the contrast to be injected at a greater rate to maximize arterial enhancement but requires high performance gradients and accurate bolus timing for all three stations. Using a 3D sequence, the time to image each station (typically ~20 s) is significantly longer than transit time of the contrast agent through that station (FOV/bolus velocity ~40 cm/5 cm/s~8 s). This reduces sharing of contrast agent between stations. As a consequence, the contrast dose required to give adequate vessel enhancement must be increased. Known MR angiography techniques use sampling according to the Nyquist sampling theorem to prevent aliasing in the MR image. However, sampling at the Nyquist rate and at the spacing interval required by the Nyquist theorem increases the acquisition time at a particular station, making it difficult to image multiple stations using a single administration of a contrast agent.

The rapid transit time of a contrast agent through the peripheral vascular anatomy also poses timing problems in other regions, such as the carotid artery. The carotid artery is one of the most common sites for athlerosclerotic vascular disease, which accounts for the majority of cerebrovascular events in western society. Although 2D and 3D time-of-flight MRA have revolutionized the evaluation of the carotid arteries, these MRA techniques have important limitations related to motion and flow artifacts, long acquisition times, and the difficulty in imaging the entire vessel down to the aortic arch. Contrast-enhanced carotid MRA, in addition to reduced scan time, also improves visualization of plaque ulcerations and improved field of view. For the carotid artery, contrast-enhanced MRA allows imaging the artery to the great vessel origins.

However, a major challenge in contrast enhanced imaging of the carotid arteries is due to rapid arterial-venous transit. The duration of the arterial-only phase (typically ~10 s) is usually substantially shorter than the acquisition time required for a high-resolution 3D dataset (~30 s).

Conventional MRA employs elliptical-centric view ordering of the k-space. This standard view order concentrates the high signal k-space center at the beginning of a scan in a region of interest. However, if the k-space center is acquired during the rising edge of arterial enhancement, reduced arterial signal intensity and arterial ringing artifacts may result. Delaying the acquisition of the k-space center (while using the conventional centric-order view) too far into the scan produces a significant venous artifact due to rapid contrast transit.

SUMMARY OF THE INVENTION

The present invention uses a variable k-space sampling method that minimizes scan time by tailoring the acquisition according to the vascular anatomy of the station, hence increasing dose sharing between stations. In particular, in a three station scan of the lower extremities (abdomen, thigh, and calf), at least the central station is sampled such that the number of samples taken is less than would be taken at the Nyquist rate. The spacing is more sparse than that required by the Nyquist sampling theorem, to prevent the well-known imaging artifact of wrap-around (aliasing). The MR images of the region of interest are duplicated. Subtraction of a pre-contrast mask removes non-enhancing tissue (ref. Wang), while the limited extent of vessels allows duplicated vessels to be removed using volume of interest imaging.

Additionally, to more accurately time data acquisition to bolus passage, preferably peak bolus passage, the k-space center is delayed into the scan interval for a region of interest, using a recessed view ordering scheme. This view ordering does not waste arterial phase time, because as the scan commences, low signal level high spatial frequency components are acquired.

BRIEF DESCRIPTION OF THE DRAWINGS

Exemplary embodiments of the invention are set forth below with reference to the attached drawings where:

FIG. 4A shows a coronal view. FIG. 4B shows a sagittal view and FIG. 4C shows a sagittal after removal of ghost image in station 2 according to an embodiment of the invention;

FIG. 6A. corresponds to projections for a conventional protocol, FIG. 6B illustrates projections for protocol with reduced anterior-posterior field-of-view in the second station according an embodiment of the present invention;

FIG. 9 illustrates examples of the extent of ringing in coronal MIPs (top) and source images (bottom). FIG. 9(a) shows no ringing visible (11% of cases), FIG. 9(b) shows moderate ringing visible in the source images (74% of cases), and FIG. 9(c) shows substantial ringing, visible in the MIP (16% of cases). Arrows indicate venous artifacts;

FIG. 10 shows a carotid study of a 62 year-old female. Oblique 2D real-time images (FIG. 10(a)) at 4 seconds, and (FIG. 10(b)) immediately prior to initiation of the 3D scan. Arrows indicate enhancement of the pulmonary arteries, aortic arch and the carotid arteries. FIG. 10(c) shows a maximum intensity projection from the subsequent coronal 3D dataset; and FIG. 11 shows a carotid study of a 74 year-old male acquired using the recessed view-ordering scheme.

DESCRIPTION OF PREFERRED EMBODIMENTS

Imaging Protocol for Peripheral Extremity Study

Figure 1:
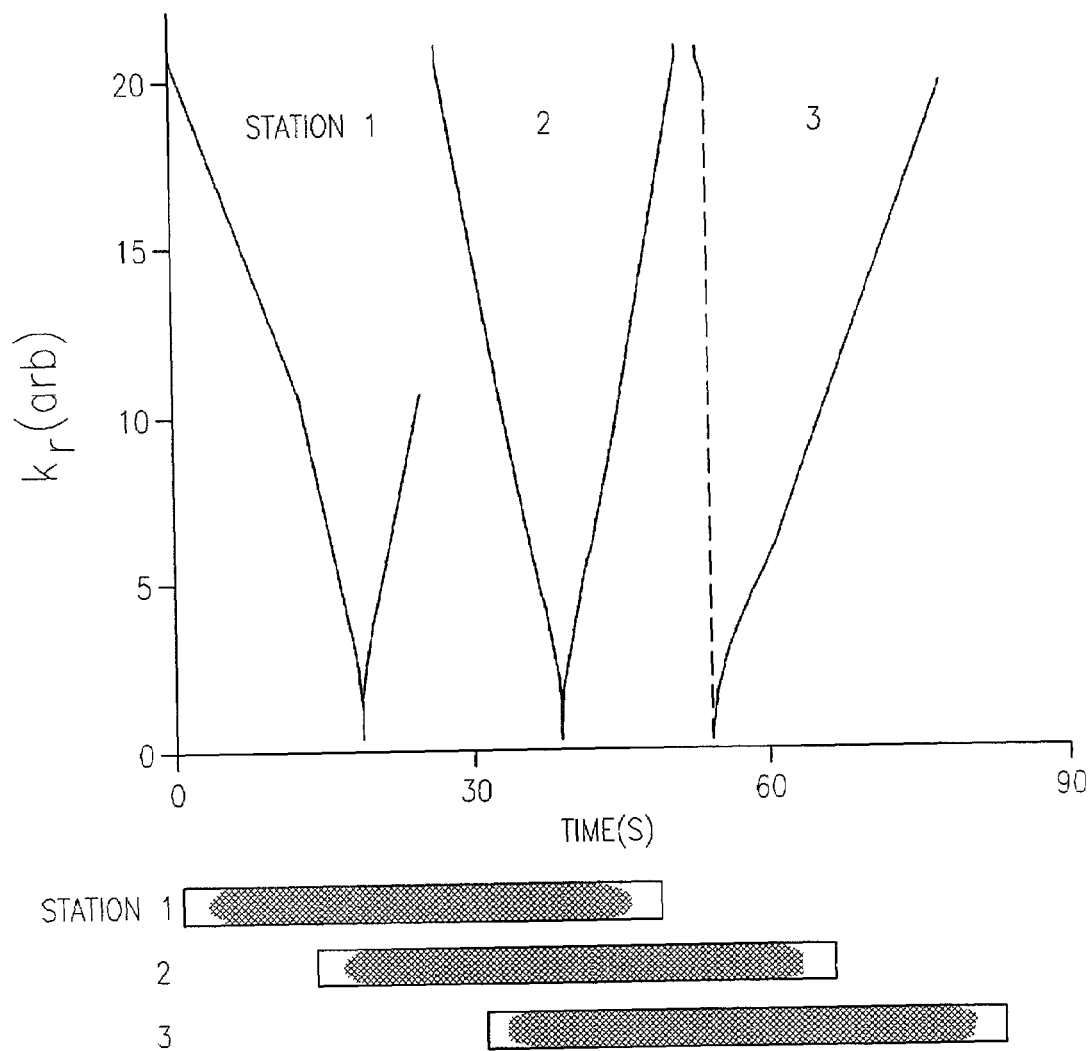
FIG. 1 is a timing diagram showing view ordering by k-space radius, $k_r$ according to a first embodiment of the present invention as applied to lower peripheral extremities.

A protocol for bolus-chase MR digital subtraction angiography according to an embodiment of the present invention was compared to the protocol used and published previously by Wang, Y., Lee, H M, Avakian R, Winchester P A, Khilnani N M, and Trost D discussed above and Lee H M, Wang Y. *Dynamic k-space filling for bolus chase 3D MR digital subtraction angiography. Magn Reson Med* 1998; 40(1):99–104.

The differences between the protocols are outlined in Table 1, and are discussed in more detail below.

TABLE 1

Summary of parameters for a conventional protocol and the inventive protocol.

| | Conventional Protocol | Inventive Protocol |
|---|---|---|
| Timing of Station 1 | Complete filling at start of acquisition | Complete filling halfway through acquisition |
| View Order for Station 1 | Edge-Center | Recessed Edge-Center |
| View Order for Station 2 | Edge-Center-Edge | Edge-Center-Edge |
| View Order for Station 3 | Center-Edge | Center-Edge |
| Reduced A/P FOV for station 2 | No | Yes |
| Receiver bandwidth | 64 kHz | 32 kHz |

The k-space sampling rate along the anterior-posterior (A/P) direction is reduced 2-fold relative to the Nyquist rate for the central station where the femoral and popliteal arteries have limited A/P extent. The rf excitation volume remains the same to ensure that all vessels are fully visible. Halving the sampling rate results in a wrap-around ghost of the vessels. Since the background is eliminated with subtraction and arteries are sparse, these effects do not cause artifacts that obstruct visualization of the arteries. The acquisition time for this station is thereby halved while maintaining resolution.

This reduced sampling could also be applied to the first and last stations, where the vascular A/P extent at any longitudinal location is still limited. However, dynamic view ordering optimally times the acquisition of the critical k-space center for the first station towards the end, and for the last station towards the beginning. Notably, the center of the k-space acquisition at the first region of interest (first station) is delayed. This modification in the shift of the k-space center acquisition is generally applicable to improve MRA for any region of interest, which will be described in more detail below. With respect to FIG. 1, the temporal separation of the centers of k-space for the three stations is thus primarily determined by the scan time of the middle station. Hence only the k-space sampling of the middle station needs to be reduced.

Timing information was provided by a test injection of 5 cc of Gd at 2 cc/s, during which coronal 2D projectional images of the central station were acquired with a temporal resolution of 1.8 s. Complex subtraction of a mask image acquired prior to the contrast arrival was used to visualize the vessels. From these data, the bolus arrival, transit and departure at the central station were determined. The timing for the bolus-chase sequence was estimated as discussed by Wang Y, Lee H M, Avakian R, Winchester P A, Khilnani N M, Trost D. *Timing algorithm for bolus chase MR digital subtraction angiography. Magn Reson Med* 1998; 39(5): 691–696. In particular, for the conventional protocol, 3D imaging of the first station was started only when the full enhancement of the entire station was observed on the timing run. For the present embodiment, the delay to the first station was chosen such that at least the last 60% of the data (the k-space center) were acquired with filling of the entire station.

A fraction of the time saved by the improved first station timing and the reduced A/P FOV was used to decrease the receiver bandwidth. This also compensated for the loss in SNR of the central station due to the reduced k-space sampling. Using the conventional protocol the 64 kHz bandwidth and 60% fraction echo gave TE/TR=1.1 ms/4.8 ms. For this embodiment, 32 kHz bandwidth gave TE/TR=1 0.3 ms/6.2 ms. The 29% increase in scan time was considered worthwhile to give a $\sqrt{2}$ improvement in SNR.

The pulse sequence was implemented on a GE Echospeed Signa MR imager, using the body coil, and is based on a standard multiphase 3D gradient echo sequence. The following imaging parameters were used: Flip angle 45°, coronal acquisition matrix of 256×192×(32–40) (corresponding to $k_x$ superior-inferior direction, $k_y$ left-right direction, and $k_z$ A/P directions respectively) with 60% fractional echo along S/I, 40 cm FOV with 0.5–0.8 phase (L/R) FOV. With these parameters, each full station was acquired in 20–30 s, and the reduced acquisition in 10–15 s.

The pulse sequence allows a user-specified view order and reduced $k_z$ (A/P) sampling for each station. Each acquisition is ordered according to k-space radius, with $k_r = \sqrt{(k_y^2 + k_z^2)}$. The view orders available for each station used were 1. edge-center, 2. center-edge, 3. edge-center-edge, or 4. edge-center, with the center recessed from the end of the scan by ¼ of the acquisition time. The latter has been found to reduce the effects of poor breathhold in the first station (abdomen) for patients with difficulty in holding their breath for the full acquisition.

The view ordering and timing of the bolus-chase sequence is illustrated schematically in FIG. 1. For the first station (abdomen), full acquisition with recessed edge-center view order; for the second (thigh) the spacing $\delta k_z$ is doubled and the number of $k_z$ samples is reduced by a factor of 2, with edge-center-edge view ordering; for the third (lower leg), full acquisition with center-edge view ordering. Using this procedure, the total temporal separation of the k-space centers for the three stations is reduced to ¾ of the full acquisition time, plus the time to move the patient between stations (approximately 2 seconds for each of the 2 repositions). With view ordering only, the corresponding temporal separation is 1¼ of the full acquisition time plus movement, and with no view ordering it is 2 full acquisitions plus reposition time.

Two repeated acquisitions for all three stations were performed. The first was a mask run, with no injection of contrast agent. The second was timed to the injection of 35–40 cc of Gd-DTPA (Magnevist, Berlex, Wayne, N.J.; Omniscan, Nycomed, Princeton, N.J.) at 1.5–2 cc/s. The total contrast dose was kept constant, and not scaled to the patient weight. Complex subtraction of the mask data from the bolus data was used to remove the background tissue signal.

The present embodiment using user selection and standard deviation plots produces about a 50% increase in signal to noise ratio without any motion correction.

The described process of sample size reduction and image processing may be implemented by software. In a second embodiment of the invention, the number of samples taken can correspond to the number of samples taken according to the Nyquist rate, but spaced further apart than in Nyquist sampling. This would extend the spatial frequency, thereby improving image resolution over standard Nyquist sampling.

Patient Studies of the Peripheral Extremities

In order to compare the present invention to a known protocol, 30 consecutive patients were recruited for evaluation of clinically suspected peripheral vascular disease at two identical MR imaging systems from October to December, 1999. The conventional protocol was used to image 16 patients at one facility (3 female, 13 male; ages 43 to 89 with a mean of 70). The method of the present invention was used for the remaining 14 (2 female, 12 male; ages 41 to 76 with a mean of 62) at the other facility. The choice of location and protocol was based on patient and referring physician preference but unrelated to medical condition. The indications leading to referral and the severity of peripheral vascular disease in the two populations are outlined in Table 2. The study was IRB approved with all patients giving informed written consent.

TABLE 2

Primary indications leading to referral, and findings for the populations undergoing the conventional and inventive protocols. Note that in all cases, one or more significant lesions were found. PTA = Percutaneous transluminal angioplasty.

|  | Conventional Protocol | Inventive Protocol |
| --- | --- | --- |
| Primary Indication |  |  |
| Claudication | 12 (75%) | 11 (78%) |
| Rest Pain/Ulceration | 3 (19%) | 2 (14%) |
| Dissection | 1 (6%) | 0 (0%) |
| Aneurysm | 0 (0%) | 1 (7%) |
| Post bypass graft or PTA/stent | 3 (19%) | 4 (29%) |
| Severity of Peripheral Vascular Disease |  |  |
| No Significant Lesions | 0 (0%) | 0 (0%) |
| One Significant Lesion | 1 (6%) | 3 (21%) |
| Multiple Significant Stenoses | 15 (94%) | 11 (79%) |

The clinical utility of the images produced depends primarily on the arterial signal enhancement due to the contrast agent, and on the background signal. The background signal may be due to noise or patient motion. Motion is particularly significant in the first station, where poor, non-reproducible breathhold and bowel gas movement can significantly reduce the effectiveness of image subtraction. In subsequent stations, patient motion is usually less significant.

Figure 2:
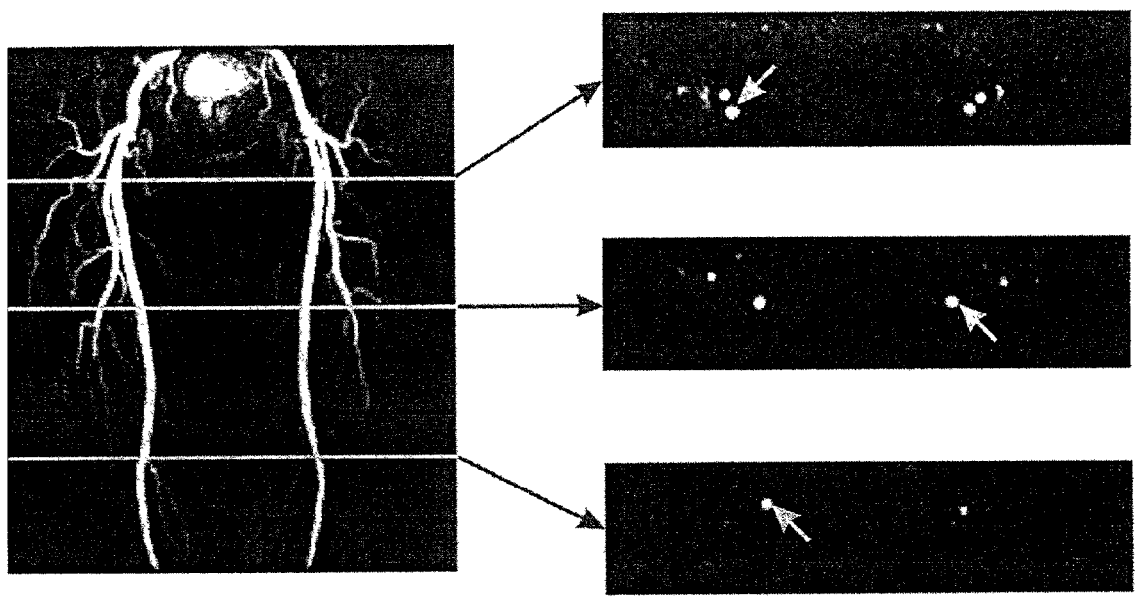
FIG. 2 shows how the statistical parameter used to evaluate the image quality is derived from arterial data.

To quantitatively assess image quality, the following procedure was used:

For each station, complex subtraction of the mask image was performed. The mean signal magnitude of the subtracted data over the entire station was calculated. Although this contains the enhanced arterial signal, the small number of voxels containing vessels allows this mean signal to be approximated as the background. For each axial slice (perpendicular to SI) in the station, the maximum signal intensity was found, which is assumed to be due to arterial enhancement. The mean peak intensity for all the slices is divided by the background to give a figure of merit for the station. This calculation is shown schematically in FIG. 2 and was automated such that no observer bias could be included. Figures of merit (FOM) were calculated for all stations of all studies. A two-sample t-test assuming unequal variances was performed on the figure of merit data from each station to evaluate the significance of the differences between the results obtained for the two protocols.

Results

Figure 3:
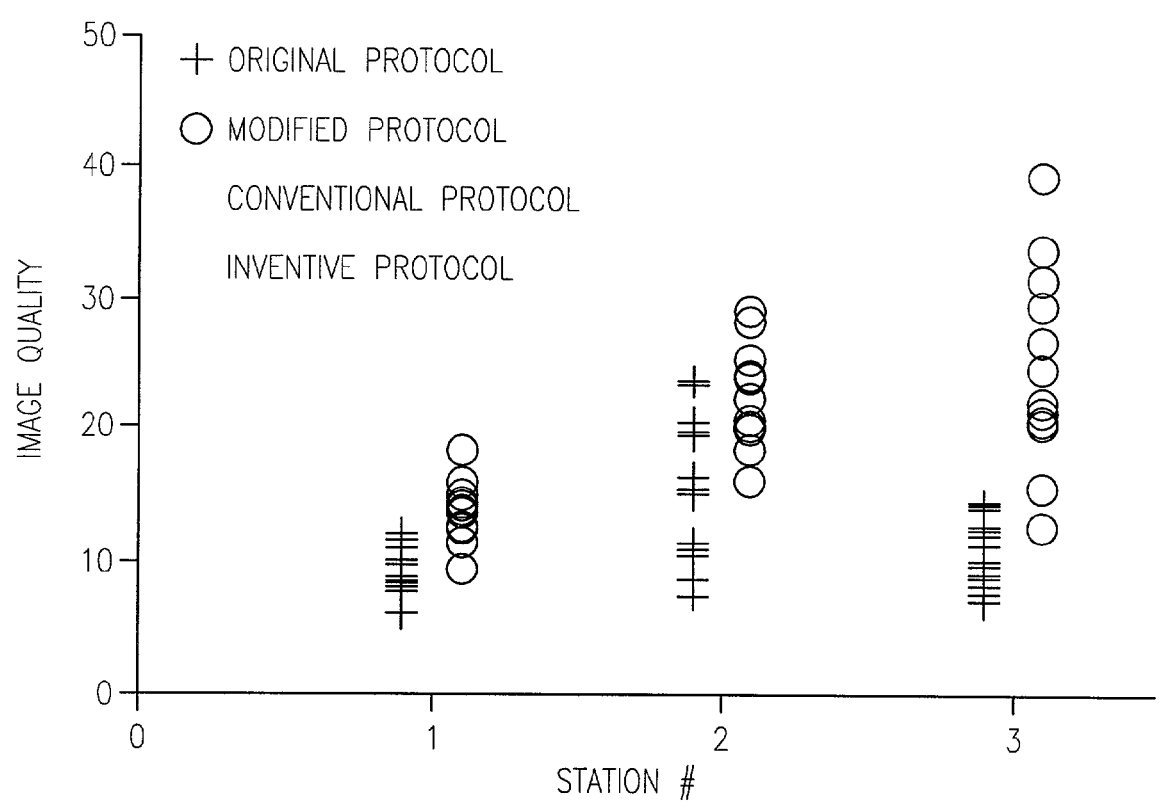
FIG. 3 shows a comparison of the image quality figures of merit obtained for all studies and stations of the peripheral extremities.

FIG. 3 shows the figure of merit data obtained from all subjects and all stations. The statistical analysis of this data is given in Table 3, showing that for all stations, significant improvement (p<0.001) was found using the inventive protocol.

TABLE 3

Figure of merit comparison for studies using the reduced FOV second station. Values quoted are x ± $\sigma_{n-1}$. p-values are calculated using a two-sample t-test assuming unequal variance.

|  | Station 1 | Station 2 | Station 3 |
| --- | --- | --- | --- |
| Conventional Protocol (n = 16) | 8.9 ± 1.6 | 15.9 ± 5.1 | 11.0 ± 2.5 |
| Inventive protocol with half FOV (n = 14) | 13.8 ± 2.22 | 22.6 ± 3.5 | 24.9 ± 7.2 |
| p | $4.1 \times 10^{-7}$ | $2.4 \times 10^{-4}$ | $3.5 \times 10^{-6}$ |

Figure 4A:
FIGS. 4A–4C illustrate maximum intensity projection (MIP) images from a 52-year old female showing claudication of the left leg.
Figure 4B:
Figure 4C:

FIG. 4 shows an example of a scan performed using the inventive protocol and the reduced A/P FOV in the second station. The study shows a patient with claudication in the left leg. The coronal view does not show the ghost image in the second station because it lies directly on top of the real image (FIG. 4a). The sagittal view shows that the ghost and real images are separated (FIG. 4b) and that the ghost can be removed using volume of interest (VOI) rendering (FIG. 4c). Once the volume of interest has been defined, projections can be made at any viewing angle. The ghost image was successfully removed from all studies using the reduced $k_z$ field of view. Additionally, removing the bladder from a coronal section was also found to be useful to improve visualization of vessels on the maximum intensity projection The high concentration of contrast agent and reduced receiver bandwidth gives excellent SNR in all three stations, while the short acquisition time gives negligible venous signal.

Figure 5:
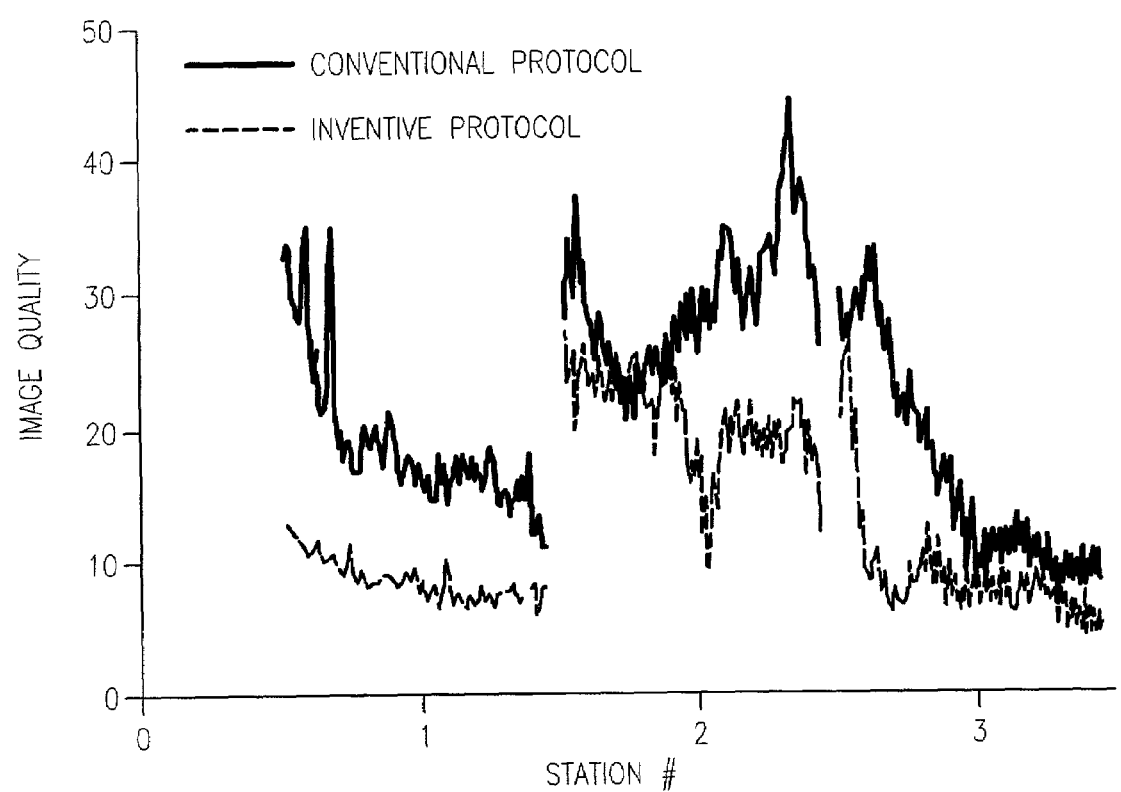
FIG. 5 illustrates the arterial signal to background ratio vs. superior-inferior position for median studies for a conventional protocol and a protocol of the present invention.
Figure 6A:
FIGS. 6A and 6B illustrate maximum intensity projections of the median data presented in FIG. 5.
Figure 6B:
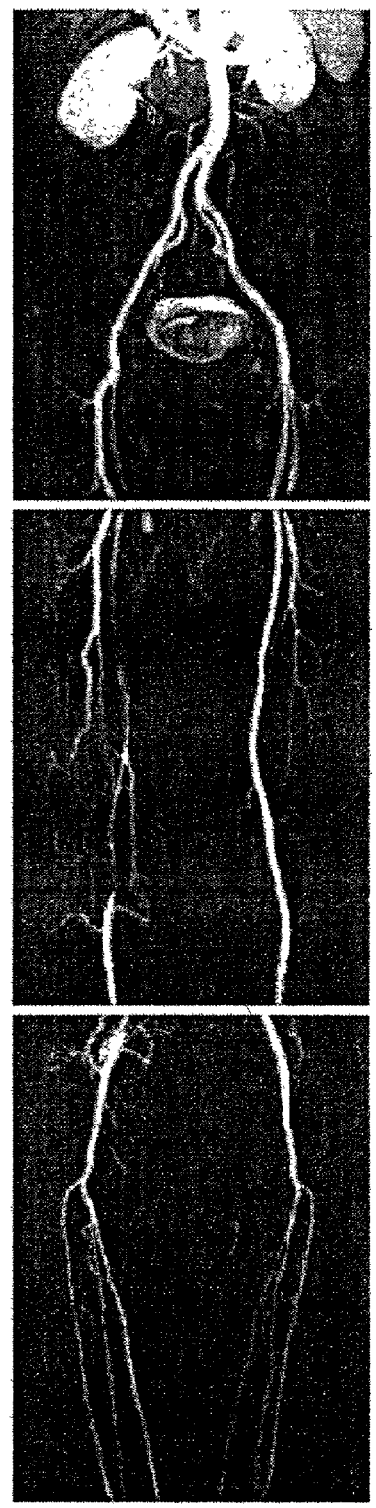

The studies with the median FOM (averaged over all stations) for the two protocols were selected, and represent typical examinations. The variation of arterial signal with SI position is shown in FIG. 5, with the corresponding images shown in FIG. 6. It can be seen in FIG. 5 that the signal to background ratio is higher for the invention in all stations. However, it should be noted that in both cases, the values for the first station are reduced due to the increased background caused by motion during the breath hold. FIG. 6A (conventional protocol) shows significantly greater motion effects than FIG. 6B (inventive protocol), possibly due to the recessed k-space center in the invention and the different timing methods.

DISCUSSION

The disclosed data demonstrates that the bolus chase protocol outlined here provides significantly higher quality images than conventionally known and used protocols. The important differences between the protocols are: improved timing of the first station; reduced A/P FOV for the second station; and reduced receiver bandwidth to give improved SNR. The improvement in image quality can be mainly attributed to better timing of the acquisition to the passage of the bolus through the arterial system, leading to more sharing of the bolus between stations.

The image quality obtained in bolus-chase studies is critically dependent on accurate timing of the arterial phase of the bolus to the acquisition of the k-space centers for each station. For three-station studies, dynamic view ordering reduces the minimum separation of the k-space centers of the three stations to the time to acquire the central station plus the time taken to move between stations. Reducing the acquisition time of central station through reducing A/P FOV improves matching of the acquisition rate to the bolus velocity. In this manner, a full high-resolution 3D volume can be acquired in the time taken for the bolus to traverse the station.

Decreasing the sampling rate along $k_z$ in the central station is an effective way to decrease the acquisition time without sacrificing resolution or spatial coverage. Exciting the same volume as the other stations ensures that all vessels are imaged. The same maximum value of $k_z$ gives the same spatial resolution as the full acquisition, but the undersampling leads to a ghost wrap-around image. The removal of the ghost image is possible because (1) subtraction of the mask removes the surrounding tissue which would otherwise be wrapped onto the vessels, and (2) the vessels have limited A/P extent, so the real and ghost images do not overlap and are separable using standard volume-of-interest rendering. As long as the vessels at any cross-sectional location are contained within half the full A/P field of view then the images will be separable. In our experience, this is universally the case in the thigh. More generally, an image volume having x, y. z orthogonal coordinates and a thickness along z=Tv, for every location x, y within the volume having a thickness $T_s < T_v$, three dimensional k space sampling may be accelerated by a factor $F \leq T_v/T_s$ by increasing the spacing of the k space sampling along $k_z$ by a factor of F while maintaining the sampling frequencies range unchanged from sampling according to the Nyquist sampling theorem to prevent the well-known imaging artifact of wrap-around (aliasing).

For the first station, acquiring only the central 60% of k-space during full arterial enhancement could lead to a reduction in the visibility of small vessels. However, in our experience, it appears that this is not a significant problem. Instead, the image quality in this station appears to be improved by the modified timing. One specific advantage is that the earlier acquisition prevents venous signal obscuring the renal arteries as discussed in Ruhm S G, Debatin J F. *Contrast-enhanced 3D MR angiography of the thorax, abdomen and lower extremities. Radiologe* 1999; 39(2): 100–109, Rofsky N M, Adelman M A. *MR Angiography in the Evaluation of Atherosclerotic Periphal Vascula Disease, Radiology* 2000; 214(2):325–338, Grist T M. *MRA of the abdominal aorta and lower extremity. J. Magn Reson Imaging* 2000; 11(1):32–43 and Prince M R, Brist T M, Debatin J F. *3D Contrast MR angiography.* Springer, Berlin. 1999.

The reduced number of $k_z$-acquisitions of the second station would be expected to reduce the SNR by a factor of $\sqrt{2}$ in that station. However, the reduced receiver bandwidth and increased arterial bolus concentration more than compensate for this loss of SNR.

It should also be noted that in some patients, the blood flow rate is significantly reduced due to aneurysms or occlusions. This can be observed during the 2D timing run. During this study, 4/18 patients (22%) scheduled to have the reduced FOV study were found to have sufficiently slow blood flow that there was a danger of the reduced FOV acquisition being faster than the bolus. In these cases, a full acquisition of the second station was used, but the data excluded from the study.

The A/P FOV of the middle station (encompassing femoral arteries) was reduced by half in this study. Potentially this A/P FOV can be further reduced for an even faster bolus chase, and could be replaced with a 2D projection acquisition as most significant stenoses in femoral arteries may be adequately visualized in the A/P projection.

Imaging Protocol for Carotid Study

To better observe the effects of a recessed center view order, additional patient studies were made using a GE Signa CVi MR scanner (General Electric Co, Milwaukee, Wis.). The study was IRB approved with all patients giving informed written consent.

In particular, to develop a better understanding of carotid contrast dynamics, a preliminary study was performed in which 22 patients were imaged using only time-resolved oblique 2D projection MRA of the aortic arch and carotid arteries. Images were obtained during a breath-hold at 1–2 second intervals using a fast 2D spoiled gradient echo sequence. The sequence parameters were: TR=7.0–9.7, TE=1.8–2.2, bandwidth 15.6–31.3, FOV 24–34 cm, slab thickness 80–140 cm. Complex subtraction of a precontrast mask was used to enhance vessel conspicuity.

The fluoroscopically triggered pulse sequence is based on a standard multiphase 3D spoiled gradient echo sequence. For 3D imaging, two different view-ordering schemes were evaluated:

1. Standard center-edge elliptical-centric;
2. A recessed center-edge elliptical-centric view order in which the very center of k-space is acquired 3 seconds into the acquisition. It is hypothesized that this view order will better time the k-space center to the peak arterial concentration prior to venous return, giving better arterial visualization.

Figure 7A:
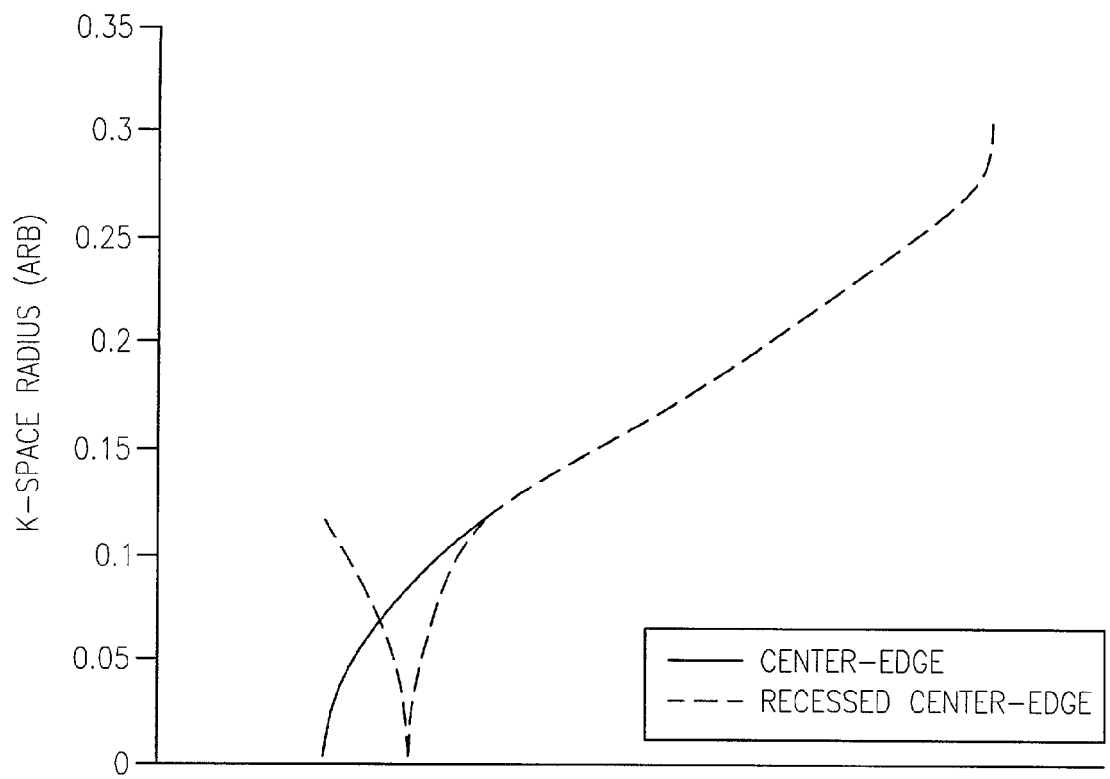
FIG. 7 illustrates a view ordering scheme (for a carotid artery), where the recessed center-edge view order (gray) better matches the acquisition of the k-space center to the peak arterial concentration prior to venous enhancement than the standard elliptical-centric acquisition (black)
Figure 7B:
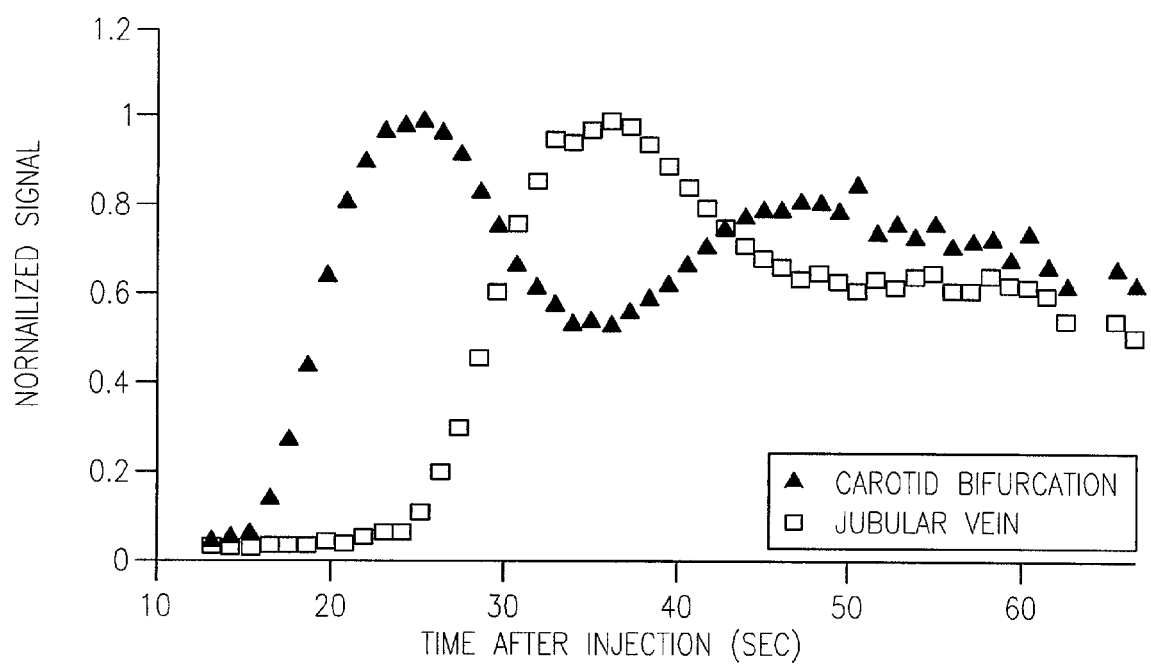

A comparative illustration of the two view ordering schemes is illustrated in the bottom portion of FIG. 7. Note that beyond the recessed region the acquisition timing is identical. The recessed view ordering of a preferred embodiment is calculated as follows:

An array of the ky-kz values to be acquired is generated and ordered according to the corresponding k-space radius, kr. The four points (ky, kz), (-ky, kz), (ky, -kz) and (-ky, kz) are degenerate, with identical values for kr. Due to the sequential nature of the insertion sort through the ky-kz array, these degenerate points are always ordered as

[1] (-ky, -kz), [2] (-ky, kz), [3] (ky, -kz) [4] (ky, kz)

For the simple elliptical-centric case, the order of acquisition is simply the order of this sorted array—the index of the array is the acquisition number. For the recessed elliptical centric case, the index of the sorted array (Index) is calculated as a function of the acquisition number n, which counts from 0, and the number of recessed acquisitions ($N_R$) using the following calculation.

| | |
|---|---|
| Index = $N_R$ - 2n - 1 | n < $N_R$/2 |
| Index = 2n - $N_R$ | $N_R$/2 ≤ n < $N_R$ |
| Index = n | n ≥ $N_R$ |

The center of the k-space is acquired when n=$N_R$/2, and for n≥$N_R$, the acquisition is identical to the elliptical-centric case. A consequence of this view ordering is that for each odd index point (in the recessed part of the acquisition) acquired at a given time prior to the k-space center, a corresponding even index is acquired at an equal amount of time after the center. With the array sorting as described, this ensures that conjugate point (ky, kz) and (-ky, -kz) are acquired at symmetric time points with respect to the k-space center.

While the above specifically contemplates the case where the k-space acquisitions in the recessed part of the acquisition are symmetric about the k-space center, the invention is more generally applicable depending of the field of view, the enhancement uptake curve and degree of recess. The amount that the radius is recessed from the center will also effect the number of acquisitions taken from the recessed point to the k-space center and the number of recessed points taken from the k-space center outwards towards the opposite recessed edge.

More generally, the algorithm for k-space recession in real-time triggered contrast enhanced MRA, which matches k-space sampling to the vessel contrast enhancement profile can be described as follows.

As one embodiment of the technique,

Let N be the total number of points in k-space $k_y k_z$.

Let $\{K[i]\} \forall i \in [0, N-1]$ be the array of k-space points ordered in ascending radius (degenerative points are ordered with increasing $k_z$ then increasing $k_y$).

Let $T_{recess}$ be the time for recessing the k-space center (determined by the duration from start of scan to the arrival of peak enhancement)

Let $k_R$ be the spatial frequency desired to start for recession (determined by the enhancement value at the start of scan), and the corresponding index in the array K[] is $N_R - 1$.

Let TR be the sequence repetition time, the time to acquire one point in the ky kz plane.

Then the number of points in k-space that can be acquired during recess time is $N_{recess} = T_{recess}/TR \leq N_R/2$.

Let $M = N_R/N_{recess}$.

The k-space recession can be performed by allocating k-space points from the array K[] using the following index assignment:

Index=$N_R - 1 - M*n$, for every $n^{th}$ point to be acquired, with n=0, 1, ..., $N_{recess} - 1$.

Once the k-space center is reached (n=$N_{recess} - 1$ and index=0), then k-space sampling is changed to center-edge manner: allocating k-space points from the remaining unsampled points in the array K[] by sequentially increasing assignment of the index from 0.

A second embodiment of the technique corresponds to the case where the contrast enhancement curve is known or estimated in advance.

Then the contrast enhancement curve C(t) (as defined by the arterial MR signal) can be digitized at the time points of data sampling to generate an array $\{C[i]\} \forall i \in [0, N-1]$.

Let $\{D[i]\} \forall i \in [0, N-1]$ be the index array that sorts array C[] in descending order, i.e., $\{C[D[i]]\} \forall i \in [0, N-1]$ is a descending array.

Then the recessed centric k-space sampling algorithm that matches the k-space sampling to the contrast enhancement curve is to allocate k-space point from the array K[] (as defined in the above embodiment 1) using the following index assignment:

Index=D[n] for the $n^{th}$ point to be acquired, with n=0, 1, ..., N-1. (N is the total number of k-space points, as defined in embodiment 1).

Summarizing this scheme, the lowest spatial frequency data is acquired at the estimated maximum contrast enhancement, the next lowest spatial frequency data at the next highest contrast and so on.

The 3D volume to be imaged is a coronal section prescribed graphically from an axial scout scan. The top portion of FIG. 7 shows the analysis of a dynamic 2D study. The arterial and venous signals were measured as a function of time after contrast injection. The arterial only phase is observed to last 8–10 seconds. Experimental data such as this may be used to accurately simulate the effects of different triggering delays in 3D acquisitions.

The following imaging parameters were used: Flip angle 45°, receive bandwidth 32 kHz, TE/TR=2.0/6.0 ms, head/neck neurovascular array coil, coronal acquisition matrix of 256×192×(24–32) (corresponding to kx S/I, ky L/R, and kz A/P directions respectively) with 60% fractional echo along S/I, 24 cm FOV. With these parameters, the 3D dataset was acquired in 20–30 s.

For 2D fluoroscopic monitoring, the same pulse sequence is used as for the 3D imaging, but with the slice-encoding gradients removed. Additionally, the 2D volume position and thickness may be interactively adjusted in real-time independently of the 3D volume. The imaging volume may be shifted in the frequency- and slice-encode directions, as well as rotated axially. The scan parameters (TR, TE, flip angle, acquisition matrix, FOV, receiver bandwidth) were otherwise identical to those used for the 3D acquisition. The update rate for an entire set of 2D Fourier data (one complete image) was approximately one second. Real-time control was achieved using an additional workstation (Sun Ultra-2, Sun Microsystems) with a fast fiber-optic link (BIT3 corporation) to the MR scanner. Using a sliding window technique, the update time for data transfer, 2D Fourier transform, and display is approximately 150 ms for a single-coil acquisition and 250 ms for a 4-coil phased-array acquisition. Sliders are used to interactively adjust the imaging volume, with a button to initiate the 3D acquisition. The delay between user initiation and the start of the 3D acquisition was 120 ms.

The fluoroscopic monitoring volume was chosen to be an oblique thick slab in the plane of the aortic arch, positioned inferior to the subsequent coronal 3D imaging volume. This allowed the contrast passage to be followed from the subclavian vein to the pulmonary arteries, pulmonary veins, left ventricle, aortic arch and finally the carotid arteries. Monitoring upstream of the anatomical volume of interest cues the operator prior to contrast arrival, and may substantially reduce operator-induced delay. Additionally, this choice of monitoring plane reduces inflow effects due to blood motion, further decreasing the likelihood of false triggering. Both the 2D and 3D data was acquired during a single injection of 20 cc of Gd-DTPA (Magnevist, Berlex, Wayne, N.J.) at 1.5 cc/s.

Patient Studies on Carotid Artery

To evaluate the utility of this protocol, 37 consecutive patients (11 female, 27 male, ages 36–91, mean 67) were recruited for evaluation of clinically suspected vascular disease. Nineteen patients were scanned using the elliptical-centric view ordering, and 18 using the recessed technique of the present invention.

To quantitatively assess the degree of venous ringing, axial cross sections were taken through the carotid bifurcation. Note that there is no ringing in the frequency-encode (superior-inferior) direction. Signal intensities from the arteries, the veins, the surrounding tissue and the background noise were measured and compared for each study. More qualitatively, the visibility of venous signal on coronal maximum intensity projections and the axial cross sections was assessed.

Results

Figure 8:
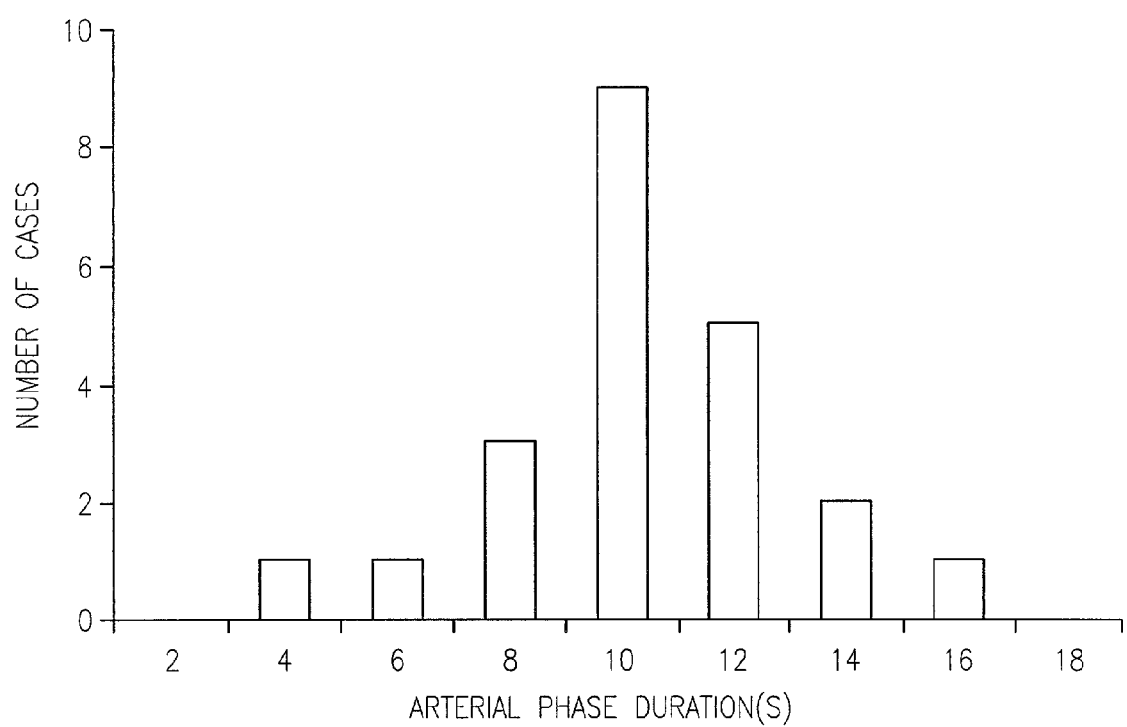
FIG. 8 is a histogram of the duration of arterial enhancement (in a carotid artery) prior to venous return in a 22 patient study, where measurements were made using time-resolved (1–2 seconds/phase) thick-slab 2D breath hold acquisitions with complex subtraction.

The distribution of the arterial phase duration for the preliminary study of 22 patients is shown in FIG. 8. The arterial-venous transit time is typically around 10 s, but there is substantial variability between patients, with values of between 4 s and 16 s.

All 37 patients (100%) scanned with the fluoroscopic technique demonstrated diagnostic MR arteriograms with sufficient arterial enhancement for the 3D acquisition. For the nineteen patients scanned using the conventional elliptical-centric view order, three (16%) showed substantial venous enhancement on coronal maximum intensity projections (MIPs). Even in these three cases, only the edges of the veins were visible, and these edges were still substantially weaker than the arteries, allowing them to be easily distinguished. In a further 14 (74%) cases, some ringing was visible on the source images, but was weak enough that it was not noticeable on the MIPs. In the remaining 2 cases (11%), no ringing was visible in either the MIPs or the source images. Volume of interest MIP rendering further enhanced arterial clarity in all cases. FIG. 9 shows a spectrum of studies with substantial, moderate and no ringing artifacts.

For the eighteen patients scanned using the recessed elliptical-centric view order, none (0%) showed substantial ringing on the MIPs. In 14 (78%) cases some ringing was visible on the source images, while in the remaining 4 (22%) cases no ringing was visible. In these studies, the ratio of mean arterial signal to peak venous signal varied from 1.5 (substantial ringing) to greater than 5, at which point the vein was difficult to distinguish from the tissue background. In general, ratios of 2 or greater were found to give good background suppression in MIP images without selected volume imaging. The ratio of mean arterial signal to peak venous signal for the elliptical-centric view order was 2.75 (standard deviation 1.48). For the recessed view order this ratio was increased to 3.07 (standard deviation 1.07). Using a one-tail t-test, the difference between the means was not significant at the 5% confidence level (p=0.23). This lack of statistical significance is likely due to the small sample size and the large inter-patient variability demonstrated in FIG. 8. However, the number of scans with ratios less than 2 was reduced from 6/19 (32%) to 1/18 (6%). Assuming a binomial distribution, this difference is significant at the 5% level.

Figure 11A:
FIG. 11(a) shows a coronal maximum intensity projection showing coverage from the aortic arch to the Circle of Willis.
Figure 11B:
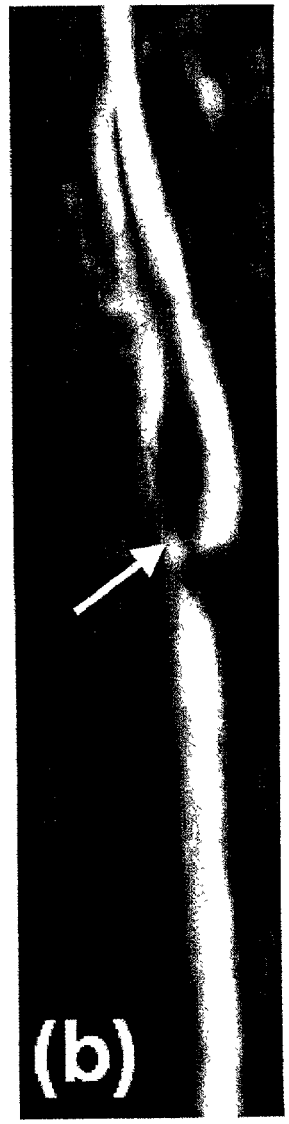
FIG. 11(b) shows selected volume oblique view showing multiple stenoses at the left carotid bifurcation.

The arterial signal intensity in all 37 cases was between 7 and 25 times greater than the signal intensity from the surrounding neck tissue. This is more than sufficient for excellent vessel conspicuity against the background tissue. FIGS. 10 and 11 show examples. In FIG. 10, 2D images prior to initiation of the 3D scan clearly show pulmonary enhancement several seconds prior to contrast reaching the aortic arch. FIG. 11 shows data from a patient with multiple stenoses at the left carotid bifurcation.

DISCUSSION

The recessed elliptical-centric view ordering scheme presented shifts the acquisition of the k-space center a few seconds into the scan. The time prior to the acquisition of the center is still used to acquire data, but not the very center of k-space. This allows the operator to initiate the scan earlier, with confidence that the k-space center will be acquired close to peak arterial enhancement and prior to venous enhancement.

If some data is acquired on the rising edge of contrast enhancement, the question remains as to whether such data will cause significant imaging artifacts. It is hypothesized that such artifacts will be minimal for two reasons.

1. The signal power in typical MRA imaging situations is strongly peaked at the k-space center.
2. The recessed acquisition order has 180° symmetry with respect to the k-space center. For each point (ky, kz) acquired prior to the center, there is a conjugate point (−ky, −kz) acquired an equal amount of time following the center.

The use of recessed elliptical-centric view ordering has been found to increase the reliability of the technique. This is reflected in our results: while the mean arterial to venous ratio is not improved to an extent that is statistically significant with this small sample size, the number of scans with poor ratios (due to reduced arterial signal) is reduced.

The intensity of the venous ringing decreases rapidly as the venous arrival is delayed later into the acquisition. Larger vessels have their signal peaked more strongly at the k-space center, so are expected to be better suppressed than smaller vessels. The rate at which k-space is traversed during the acquisition depends inversely on the field of view chosen. In this study, a large field of view of ~30 cm is used to image from the aortic arch to the Circle of Willis, making this particularly susceptible to venous contamination.

High contrast to noise ratios (CNR) were obtained in all cases. This suggests that it would be possible to increase the scan resolution while still maintaining sufficient CNR for vessel conspicuity. A further study is underway in which the acquisition matrix size in the frequency encode (superior-inferior) direction is doubled. Additionally, increasing the frame rate for the fluoroscopic part of the acquisition may be achieved by acquiring fewer phase encodes for each fluoroscopic image. Since high resolution is not required for monitoring of the aortic arch, increasing temporal resolution at the cost of decreased spatial resolution would seem worthwhile.

CONCLUSIONS

An improved bolus chase MR digital substation angiography technique is developed that consistently provides high quality angiograms of the arterial system from the abdomen to the calf. The robustness against poor breath-hold during imaging the abdomen region is maintained with recessed reverse centric view order. The reduced A/P FOV, through modified k-space spacing, allows effective chasing and maximum sharing of the bolus. With optimal timing at the start of abdomen station, the calf station is reliably imaged with adequate SNR and minimal venous signal. This protocol described here with reduced $k_z$-sampling has been incorporated into our routine clinical practice.

In addition, contrast-enhanced 3D MRA has been shown to be a fast, reliable, and clinically useful. The recessed elliptical-centric view-ordering scheme disclosed above better times the acquisition of k-space center to peak arterial enhancement. It is more robust to timing errors than conventional elliptical-centric view-ordering, allowing triggering the scan at the start of contrast arrival. This permits substantially more of the arterial-only phase to be utilized, resulting in less venous signal.

While preferred embodiments of the invention have been described above, one skilled in the art would understand that modifications may be made thereto without departing from the spirit and scope of the invention. For instance, while the invention has been discussed with respect to lower extremities and carotid artery, other body parts may be imaged using the inventive method and apparatus.

What is claimed is:

1. A method of accelerating volumetric MR imaging of arteries or other structures comprising the following:

a) an image volume having x, y and z orthogonal coordinates and a thickness along z=Tv;
   b) for every x, y location within the volume the structures to be imaged have a thickness Ts<Tv;
   c) three-dimensional k space sampling is accelerated by a factor F≦Tv/Ts by increasing the spacing of k space sampling along kz by a factor of F while maintaining the sampling spatial frequency ranges unchanged;
   d) reconstruct with 3-D Fourier Transformation utilizing a field of view in the z direction which is equal to Tv/F;
   e) create 1/F duplicate copies of the reconstructed volumetric data and stacked together adjacent to each other in the z direction; and
   f) post-process the combined multiple copies of volumetric data to select a subset of the total combined volume containing a single complete data set of the structures of interest.

2. The method of claim 1 in which the data is shifted in z prior to creating multiple copies so as to make step f) easier to perform.

3. A method of increasing the resolution of volumetric MR imaging of arteries or other structures comprising the following:

a) an image volume having x, y and z orthogonal coordinates and a thickness along z=Tv
   b) for every x, y location within the volume the structures to be imaged have a thickness Ts<Tv
   c) increase the maximum spatial frequency sampled by a factor F≦Tv/Ts by increasing the spacing of k space sampling along kz by a factor of F while maintaining the same total acquisition time
   d) reconstruct with 3-D Fourier Transformation utilizing a field of view in the z direction which is equal to Tv/F
   e) create 1/F duplicate copies of the reconstructed volumetric data and stacked together adjacent to each other in the z direction
   f) post-process the combined multiple copies of volumetric data to select a subset of the total combined volume containing a single complete data set of the structures of interest.

4. A method of 3-D gradient echo MR imaging of the abdomen, pelvis and leg arteries of a patient lying on a moveable table in an MR imaging apparatus during a single injection of contrast agent comprising the following:

a first station positioned to image abdominal and pelvis arteries with k space sampling starting at the edge of k space and the center of k space sampled during the second half of the acquisition; sampling of the center of k space is timed to coincide with contrast passing through the abdomen and pelvis arteries;
   a second station positioned to image thigh arteries accelerated with the method of any one of claims 1–2 with table movement and timing of the sampling of the center of k-space to coincide with contrast passing through the thigh arteries;
   a third station positioned to image calf arteries in which the center of k space is sampled near the beginning of the acquisition with table movement and timing of the sampling of the center of k-space to coincide with contrast passing through the calf arteries.

5. Method of claim 4 in which the center of k space for the first station is sampled approximately ¾ the way into the scan.

6. Method of claim 5 in which the third station is performed with a method comprising:

a) applying a static magnetic field to the region of interest;
b) applying a magnetic gradient along at least first and second dimensions to produce a spatially distributed magnetic response of varying frequency and varying magnitude;
c) sampling the magnetic response at a spacing interval corresponding to a sampling rate which is less than a Nyguist rate;
d) performing a Fourier transform on the result of step (c) to provide a first imaging result;
e) providing a duplicate of image information of the first imaging result to provide a second imaging result; and
f) combining the first and second imaging results to isolate arterial features in the region of interest;

and there is a fourth station which has a center k space sampled toward the beginning of the scan with table movement and timing of the sampling of the center of k-space to coincide with contrast passing through the arteries of that station.

7. A method of MR imaging a region of interest comprising:
administering a contrast agent to the region of interest;
applying a static magnetic field to the region of interest;
applying a magnetic gradient along at least one of first and second dimensions to produce a distributed magnetic response having a spatial distribution in k-space;
sampling the magnetic response, wherein sampling is performed such that sampling of a center of the k-space is delayed from a start of sampling of the magnetic response, such that sampling of the center of the k-space is timed to coincide with a substantial peak of the contrast agent passing through the region of interest;
wherein the sampling of the k-space center is preceded by sampling of a recessed-edge of k-space;
wherein the sampling of k-space center is followed by sampling of an edge of k-space substantially corresponding to a maximum spatial frequency of the magnetic response in said region of interest;
wherein a first time interval separates sampling of the k-space center and the recessed edge of the k-space and a second time interval separates sampling of k-space center and the edge of the k-space, wherein during the first time interval, sampling occurs in decreasing order of k-space radius from the recessed edge to the k-space center while sampling every Mth point (M>1), and wherein during the second time interval, sampling occurs in increasing order of k-space radius to sample each k-space point not sampled during the first time interval.

8. A method of MR imaging a region of interest comprising:
administering a contrast agent to the region of interest;
applying a static magnetic field to the region of interest;
applying a magnetic gradient along at least one of first and second dimensions to produce a distributed magnetic response having a spatial distribution in k-space;
sampling the magnetic response, wherein sampling is performed such that sampling of a center of the k-space is delayed from a start of sampling of the magnetic response, such that sampling of the center of the k-space is timed to coincide with a substantial peak of the contrast agent passing through the region of interest;
wherein sampling the magnetic response produces N points, said method further comprising:
forming an array [K] of said N points ordered in said array in order of ascending radius from the center of the k-space using index N;
setting a recessed radius $k_R$ having a corresponding index $N_R-1$ in said array to start said sampling;
setting a recess time $T_{recess}$ corresponding to a time between start of sampling and peak contrast agent in the region of interest;
setting a sequence repetition time $T_R$ as a time to acquire one sample;
wherein sampling order of the k-space prior to sampling of the k-space center is determined according to Index=$N_R-1-(N_R/(T_{recess}/TR))*n$ for $n$, $0 \leq n < (T_{recess}/TR)$.

9. The method of claim 8, wherein $(N_R/(T_{recess}/TR))=2$.

10. A method of MR imaging a region of interest comprising:
a) administering a contrast agent to the region of interest;
b) applying a static magnetic field to the region of interest;
c) applying a magnetic gradient along at least one of first and second dimensions to produce a distributed magnetic response having a spatial distribution in k-space including a low spatial frequency, an intermediate spatial frequency and a high spatial frequency;
d) sampling the magnetic response in order of the intermediate frequency, the low spatial frequency and the high spatial frequency, said high spatial frequency corresponding to a maximum radius value of the magnetic response in the k-space for said region of interest;
wherein a first time interval separates sampling of the intermediate spatial frequency and the low spatial frequency, and a second time interval separates sampling of the low spatial frequency and the high spatial frequency, wherein during the first time interval, sampling occurs in decreasing order of spatial frequency from the intermediate spatial frequency to the low spatial frequency, sampling every Mth point (M>1), and wherein during the second time interval, sampling occurs in increasing order of spatial frequency to sample each point not sampled during the first time interval.

11. A method of MR imaging a region of interest comprising:
a) administering a contrast agent to the region of interest;
b) applying a static magnetic field to the region of interest;
c) applying a magnetic gradient along at least one of first and second dimensions to produce a distributed magnetic response having a spatial distribution in k-space including a low spatial frequency, an intermediate spatial frequency and a high spatial frequency;
d) sampling the magnetic response in order of the intermediate frequency, the low spatial frequency and the high spatial frequency, said high spatial frequency corresponding to a maximum radius value of the magnetic response in the k-space for said region of interest;
wherein the sampling of the low spatial frequency substantially corresponds to a peak of the contrast agent passing through the region of interest.

12. A method of MR imaging a region of interest comprising:
a) administering a contrast agent to the region of interest;
b) applying a static magnetic field to the region of interest;
c) applying a magnetic gradient along at least one of first and second dimensions to produce a distributed magnetic response having a spatial distribution in k-space including a low spatial frequency, an intermediate spatial frequency and a high spatial frequency;

d) sampling the magnetic response in order of the intermediate frequency, the low spatial frequency and the high spatial frequency, said high spatial frequency corresponding to a maximum radius value of the magnetic response in the k-space for said region of interest;

wherein sampling the magnetic response produces N points, said method further comprising:

forming an array [K] of said N points ordered in said array in order of ascending radius from the center of the k-space using index N;

setting a recessed radius $k_R$ having a corresponding index $N_R-1$ in said array to start said sampling;

setting a recess time $T_{recess}$ corresponding to a time between start of sampling and peak contrast agent in the region of interest;

setting a sequence repetition time $T_R$ as a time to acquire one sample;

wherein sampling order of the k-space prior to sampling of the k-space center is determined according to $$\text{Index} = N_R - 1 - (N_R/(T_{recess}/TR))*n \text{ for } n, \ 0 \leq n < (T_{recess}/TR).$$

13. The method of claim 12, wherein $(N_R/(T_{recess}/TR))=2$.

* * * * *

UNITED STATES PATENT AND TRADEMARK OFFICE
CERTIFICATE OF CORRECTION

PATENT NO. : 7,003,343 B2 Page 1 of 1
APPLICATION NO. : 10/109888
DATED : February 21, 2006
INVENTOR(S) : Watts et al.

It is certified that error appears in the above-identified patent and that said Letters Patent is hereby corrected as shown below:

On the title page, in field (56), under "Other Publications", in column 2, line 2, after "Angiography,"" delete ",".

On the title page, in field (56), under "Other Publications", in column 2, line 3, delete "pp" and insert -- pp. --, therefor.

On page 2, in field (56), under "Other Publications", in column 2, line 2, delete "Magn" and insert -- Magn. --, therefor.

In column 15, line 8, in Claim 6, delete "Nyguist" and insert -- Nyquist --, therefor.

In column 15, line 9, in Claim 6, delete "(c)" and insert -- c) --, therefor.

In column 15, line 36, in Claim 7, delete "recessed-edge" and insert -- recessed edge --, therefor.

Signed and Sealed this

First Day of August, 2006

JON W. DUDAS
*Director of the United States Patent and Trademark Office*